US007089052B2

(12) United States Patent
Kodama et al.

(10) Patent No.: US 7,089,052 B2
(45) Date of Patent: Aug. 8, 2006

(54) METHOD AND SYSTEM FOR ESTIMATING VISCERAL FAT AREA

(75) Inventors: Miyuki Kodama, Tokyo (JP); Steven B Heymsfield, Mt. Kisco, NY (US)

(73) Assignee: Tanita Corporation, Tokyo (JP)

( * ) Notice: Subject to any disclaimer, the term of this patent is extended or adjusted under 35 U.S.C. 154(b) by 166 days.

(21) Appl. No.: 10/786,071

(22) Filed: Feb. 26, 2004

(65) Prior Publication Data

US 2005/0192509 A1    Sep. 1, 2005

(51) Int. Cl.
*A61B 5/05* (2006.01)
(52) U.S. Cl. ..................... 600/547; 600/300
(58) Field of Classification Search ............ None
See application file for complete search history.

(56) References Cited

U.S. PATENT DOCUMENTS 6,752,760 B1 * 6/2004 Kouou ................ 600/301
6,905,464 B1 * 6/2005 Kawanishi et al. ......... 600/301

2002/0111559 A1 * 8/2002 Kurata et al. ............ 600/547
2002/0151803 A1 * 10/2002 Kouou ................ 600/483

FOREIGN PATENT DOCUMENTS

JP    2003-024303    1/2003

OTHER PUBLICATIONS

U.S. Appl. No. 10/193,281.

* cited by examiner

*Primary Examiner*—Robert L. Nasser
*Assistant Examiner*—Patricia C. Mallari
(74) *Attorney, Agent, or Firm*—McDermott Will & Emery LLP

(57) ABSTRACT

A method and a system for estimating visceral fat area (VFA) of a subject uses the product of the Xth power of a height value (Ht) and the Yth power of a fat mass value (FM), through a parameter expressed as $FM/Ht^2$ or $Ht^2/FM$, or by using an equation expressed as $VFA = C11*FM/Ht^2 + C12*Age + C13$, where each of X and Y are a number other than zero. The method and the system decrease estimation errors due to height, thereby enabling common use by a number of nations each having a different average height, and decreasing cost of development and manufacturing.

14 Claims, 18 Drawing Sheets

| | | |
|---|---|---|
| HEIGHT | 888.8 | cm |
| AGE | 888.8 | YEARS OLD |
| BODY WEIGHT | 888.8 | kg |
| PERCENT BODY FAT | 888.8 | % |
| FAT MASS | 888.8 | kg |
| VISCERAL FAT AREA | 888.8 | cm² |

FIG. 12

RESULTS OF MEASUREMENTS

| SEX : MALE | AGE : XX YEARS OLD | HEIGHT : YYY cm |
|---|---|---|
| BODY WEIGHT : 56.0kg | AVERAGE BODY WEIGHT : 54.0kg | BMI : 23.7 |

| PERCENT BODY FAT : 20.5% | | PROPER RANGES | PERCENT FAT : 17.0~23.0% |
|---|---|---|---|
| FAT MASS : 18.0kg | FAT FREE MASS : 52.0kg | | FAT MASS : 9.9~14.4kg |

| | RIGHT HAND | RIGHT FOOT | LEFT HAND | LEFT FOOT | TRUNK |
|---|---|---|---|---|---|
| IMPEDANCE | | | | | |
| PARTIAL PERCENT BODY FAT | | | | | |
| PARTIAL FAT MASS | | | | | |

VISCERAL FAT AREA

FIG. 16

METHOD AND SYSTEM FOR ESTIMATING VISCERAL FAT AREA

BACKGROUND OF THE INVENTION (i) Field of the Invention

The present invention relates to a method and system for estimating a visceral fat area. More specifically, it relates to a method and system for estimating a visceral fat area of a subject based on height and fat mass of the subject.

(ii) Description of the Related Art

In recent years, accumulation of visceral fat has been receiving attention as a factor which exerts a significant influence on health and causes the onset of lifestyle-related disease. One method for estimating visceral fat area is by means of X-ray CT. However, to practice this method, the assistance of a radiological technician is essential due to the use of X-rays. This prevents the method from being widely used. Further, this method is disadvantageous in that it requires the subject to be exposed to X-rays. In addition, operation costs are excessively high.

There is a correlation between abdominal circumference on a navel and visceral fat area, and there is a method for estimating visceral fat area by use of the correlation. However, a measurement value of abdominal circumference on the navel is significantly influenced by where the circumference is measured, the degree of tension in the abdomen, the timing of the measurement, i.e., before or after a meal, and the condition of the subject, such as the position of the subject. Therefore, when visceral fat area is to be estimated based on only this measurement value or with emphasis on this measurement value, the estimation is liable to be influenced by the above measurement conditions. Further, when a subject tries to measure abdominal circumference on a navel by himself/herself, the subject is liable to tense his/her abdomen at the time of the measurement or make the measurement at an improper position.

In order to resolve such weak points in the known methods as mentioned above, one of the present inventors have invented a method and system for estimating the visceral fat area of a subject by using certain equation(s) which takes height, weight, fat mass and age of the subject as parameters, and filed as Japanese Patent Application No. 2001-212790 (Japanese Patent Publication No. 2003-24303) and U.S. patent application Ser. No. 10/193,281. However, it has been found in subsequent research of the present inventors that errors often occur in estimation of visceral fat area of a tall subject using these equation(s), because fat mass is directly used as an explanation variable in the equation(s), even if it includes a correction term of height.

FIG. 18A shows a correlation graph between fat mass measured using the well known Bioelectrical Impedance Analysis (hereinafter referred to as the "BIA") in the horizontal axis and visceral fat area measured using X-ray CT in the vertical axis. Measured data of numbers of subjects are plotted in the graph; in particular the measured data of tall subjects over 180 cm are plotted as ■ mark. The line in the graph means an equation for estimating visceral fat area using the parameter of fat mass as an explanation variable, which is acquired from the measured data. In case of the tall subjects, visceral fat area estimated using the equation is far different from the same fat area measured by using X-ray CT.

FIG. 18B shows a correlation graph between body fat percentage measured using the BIA in the horizontal axis and visceral fat area measured using X-ray CT in the vertical axis. The line in the graph represents an equation for estimating visceral fat area using a parameter of body fat percentage as an explanation variable. In case of the tall subjects, visceral fat area estimated by using this equation is far different from the same fat area measured by using the X-ray CT.

Estimation errors for tall subjects may prevent a plurality of nations, each having a different average height, from using a common equation for estimating visceral fat area. Therefore, it is necessary to prepare methods and systems for estimating visceral fat area for each nation, thereby increasing the costs of development and manufacturing.

SUMMARY OF THE INVENTION

An object of the present invention is to provide a method and system for estimating a visceral fat area that decreases the estimation errors due to height, and with which anyone can estimate a visceral fat area securely without concern for exposure to X-rays, at a low cost, and with proper accuracy.

According to one aspect of the present invention, there is provided a method for estimating visceral fat area of a subject comprising the steps of acquiring predetermined biological data of the subject including at least values each indicating height and fat mass of the subject, and estimating a value indicating visceral fat area of the subject based on the acquired biological data, wherein the estimation of the value indicating visceral fat area is performed using the product of the Xth power of the height value and the Yth power of the fat mass value, where each of X and Y is a number other than zero.

According to one embodiment of the present invention, there is provided the method mentioned above, wherein the estimation of the value indicating visceral fat area is performed by using a parameter expressed as $FM/Ht^2$, where Ht is the value indicating height and FM is the value indicating fat mass.

According to another embodiment of the present invention, there is provided the method mentioned above, wherein the estimation of the value indicating visceral fat area is performed by using a parameter expressed as $Ht^2/FM$, where Ht is the value indicating height and FM is the value indicating fat mass.

According to a further embodiment of the present invention, there is provided the method mentioned above, wherein a value indicating age of the subject is further acquired in the step of acquiring the biological data and wherein the estimation of the value indicating visceral fat area is performed by using an equation (1) as follows:

$$VFA = C11*FM/Ht^2 + C12*Age + C13 \quad (1)$$

where VFA is the value indicating visceral fat mass, Age is the value indicating age, and C11, C12 and C13 are constants.

According to another embodiment of the present invention, there is provided the method mentioned above, wherein a value indicating age of the subject is further acquired in the step of acquiring the biological data and wherein the estimation of the value indicating visceral fat area is performed by using an equation (2) as follows:

$$VFA = C21*Ht^2/FM + C22*Age + C23 \quad (2)$$

where VFA is the value indicating visceral fat mass, Age is the value indicating age, and C21, C22 and C23 are constants.

According to another embodiment of the present invention, there is provided the method mentioned above, wherein values indicating age and weight of the subject are further acquired in the step of acquiring the biological data and wherein the estimation of the value indicating visceral fat area is performed by using an equation (3) as follows:

$$VFA = C31*FM/Ht^2 + C32*Age + C33*Wt/Ht^2 + C34 \quad (3)$$

where VFA is the value indicating visceral fat mass, Age is the value indicating age, Wt is the value indicating weight, and C31, C32, C33 and C34 are constants.

According to another embodiment of the present invention, there is provided the method mentioned above, wherein values indicating age and weight of the subject are further acquired in the step of acquiring the biological data and wherein the estimation of the value indicating visceral fat area is performed by using an equation (4) as follows:

$$VFA = C41*Ht^2/FM + C42*Age + C43*Wt/Ht^2 + C44 \quad (4)$$

where VFA is the value indicating visceral fat mass, Age is the value indicating age, Wt is the value indicating weight, and C41, C42, C43 and C44 are constants.

According to another embodiment of the present invention, there is provided the method mentioned above, wherein values indicating age and body fat percentage of the subject are further acquired in the step of acquiring the biological data and wherein the estimation of the value indicating visceral fat area is performed by using an equation (5) as follows:

$$VFA = C51*FM/Ht^2 + C52*Age + C53*\% FAT + C54 \quad (5)$$

where VFA is the value indicating visceral fat mass, Age is the value indicating age, % FAT is the value indicating body fat percentage, and C51, C52, C53 and C54 are constants.

According to another embodiment of the present invention, there is provided the method mentioned above, wherein values indicating age and body fat percentage of the subject are further acquired in the step of acquiring the biological data and wherein the estimation of the value indicating visceral fat area is performed by using an equation (6) as follows:

$$VFA = C61*Ht^2/FM + C62*Age + C63*\% FAT + C64 \quad (6)$$

where VFA is the value indicating visceral fat mass, Age is the value indicating age, % FAT is the value indicating body fat percentage, and C61, C62, C63 and C64 are constants.

According to a further embodiment of the present invention, there is provided the method mentioned above, wherein the value indicating fat mass of the subject is acquired by using BIA (Bioelectrical Impedance Analysis) in the step of acquiring the biological data.

According to another aspect of the present invention, there is provided a system for estimating visceral fat area of a subject comprising a data acquiring component for acquiring predetermined biological data of the subject including at least values each indicating height and fat mass of the subject and a data processing component for estimating a value indicating visceral fat area of the subject based on the acquired biological data, wherein the data processing component estimates the value indicating visceral fat area by using the product of an Xth power of the height value and a Yth power of the fat mass value, where each of the X and the Y is a number other than zero.

According to one embodiment of the present invention, there is provided the system mentioned above, wherein the data processing component estimates the value indicating visceral fat area by using a parameter expressed as $FM/Ht^2$, where the Ht is the value indicating height and FM is the value indicating fat mass.

According to another embodiment of the present invention, there is provided the system mentioned above, wherein the data processing component estimates the value indicating visceral fat area by using a parameter expressed as $Ht^2/FM$, where Ht is the value indicating height and FM is the value indicating fat mass.

According to a further embodiment of the present invention, there is provided the system mentioned above, wherein the data acquiring component further acquires a value indicating age of the subject and wherein the data processing component estimates the value indicating visceral fat area by using an equation (1) as follows:

$$VFA = C11*FM/Ht^2 + C12*Age + C13 \quad (1)$$

where VFA is the value indicating visceral fat mass, Age is the value indicating age, and C11, C12 and C13 are constants.

According to another embodiment of the present invention, there is provided the system mentioned above, wherein the data acquiring component further acquires a value indicating age of the subject and wherein the data processing component estimates the value indicating visceral fat area by using an equation (2) as follows:

$$VFA = C21*Ht^2/FM + C22*Age + C23 \quad (2)$$

where VFA is the value indicating visceral fat mass, Age is the value indicating age, and C21, C22 and C23 are constants.

According to another embodiment of the present invention, there is provided the system mentioned above, wherein the data acquiring component further acquires values indicating age and weight of the subject and wherein the data processing component estimates the value indicating visceral fat area by using an equation (3) as follows:

$$VFA = C31*FM/Ht^2 + C32*Age + C33*Wt/Ht^2 + C34 \quad (3)$$

where VFA is the value indicating visceral fat mass, Age is the value indicating age, Wt is the value indicating weight, and C31, C32, C33 and C34 are constants.

According to another embodiment of the present invention, there is provided the system mentioned above, wherein the data acquiring component further acquires values each indicating age and weight of the subject and wherein the data processing component estimates the value indicating visceral fat area by using an equation (4) as follows:

$$VFA = C41*Ht^2/FM + C42*Age + C43*Wt/Ht^2 + C44 \quad (4)$$

where VFA is the value indicating visceral fat mass, Age is the value indicating age, Wt is the value indicating weight, and C41, C42, C43 and C44 are constants.

According to another embodiment of the present invention, there is provided the system mentioned above, wherein the data acquiring component further acquires values indicating age and body fat percentage of the subject and wherein the data processing component estimates the value indicating visceral fat area by using an equation (5) as follows:

$$VFA = C51*FM/Ht^2 + C52*Age + C53*\% FAT + C54 \quad (5)$$

where VFA is the value indicating visceral fat mass, Age is the value indicating age, % FAT is the value indicating body fat percentage, and C51, C52, C53 and C54 are constants.

According to another embodiment of the present invention, there is provided the system mentioned above, wherein the data acquiring component further acquires values indicating age and body fat percentage of the subject and wherein the data processing component estimates the value indicating visceral fat area by using an equation (6) as follows:

$$VFA = C61*Ht^2/FM + C62*Age + C63* \%FAT + C64 \qquad (6)$$

where VFA is the value indicating visceral fat mass, Age is the value indicating age, %FAT is the value indicating body fat percentage, and C61, C62, C63 and C64 are constants.

According to a further embodiment of the present invention, there is provided the system mentioned above, wherein the value indicating fat mass of the subject is acquired by the data acquiring component based on BIA (Bioelectrical Impedance Analysis).

BRIEF DESCRIPTION OF THE DRAWINGS

FIG. 12 is an example of a display of the system of FIG. 9.

FIG. 16 is an example of a display of the system of FIG. 13A.

DETAILED DESCRIPTION

Embodiments of the present invention will be described in detail with reference to the attached drawings.

Firstly, a method for estimating a visceral fat area which underlies the present invention will be described.

It has been found in recent research of the present inventors that visceral fat area correlates closely with a parameter of corrected fat mass directly by height. The present invention provides a method for estimating a visceral fat area relying upon the correlation, in particular by using the product of the Xth power of the height value and the Yth power of the fat mass value, where X and Y each is a number other than zero.

The present inventors measured height (Ht), fat mass (FM) and visceral fat area (VFA) of a number of subjects, and then worked out a natural logarithm equation as expressed LN(VFA)=X*Ht+Y*FM by substituting the measured data for the equation to determine the numbers applicable to X and Y. BIA was used for measuring the fat mass of the subjects, and X-ray CT was used for measuring the visceral fat area of the subjects.

Figure 1:
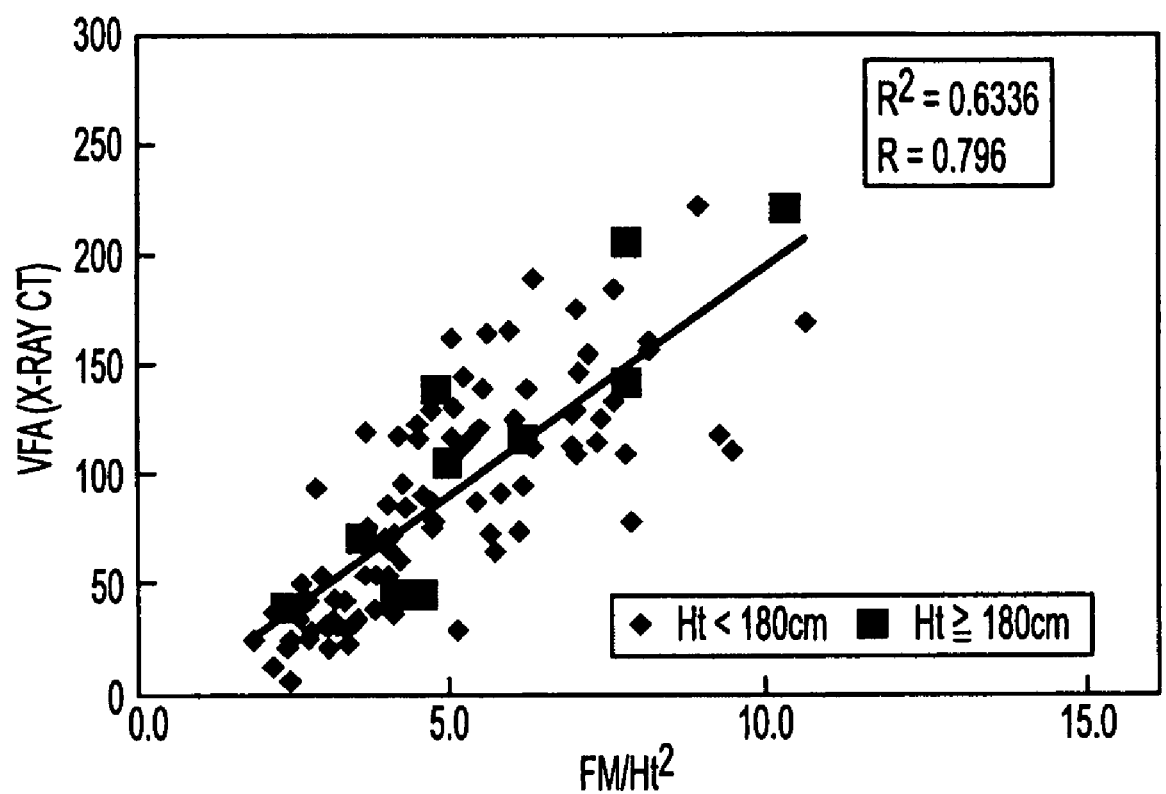
FIG. 1 is a graph showing a correlation between the parameter $FM/Ht^2$ and a visceral fat area measured by X-ray CT.

As a result of this effort, −2 and 1 were determined as applicable numbers for each of X and Y. In this regard, it has been confirmed as shown in FIG. 1 that the visceral fat area (VFA) correlates closely with a parameter $FM/Ht^2$ (where, X=−2 and Y=1), regardless of height of the subjects. Therefore, estimation of visceral fat area by using a parameter expressed as $FM/Ht^2$ is desirable and preferable for decreasing estimation errors due to height.

Figure 2:
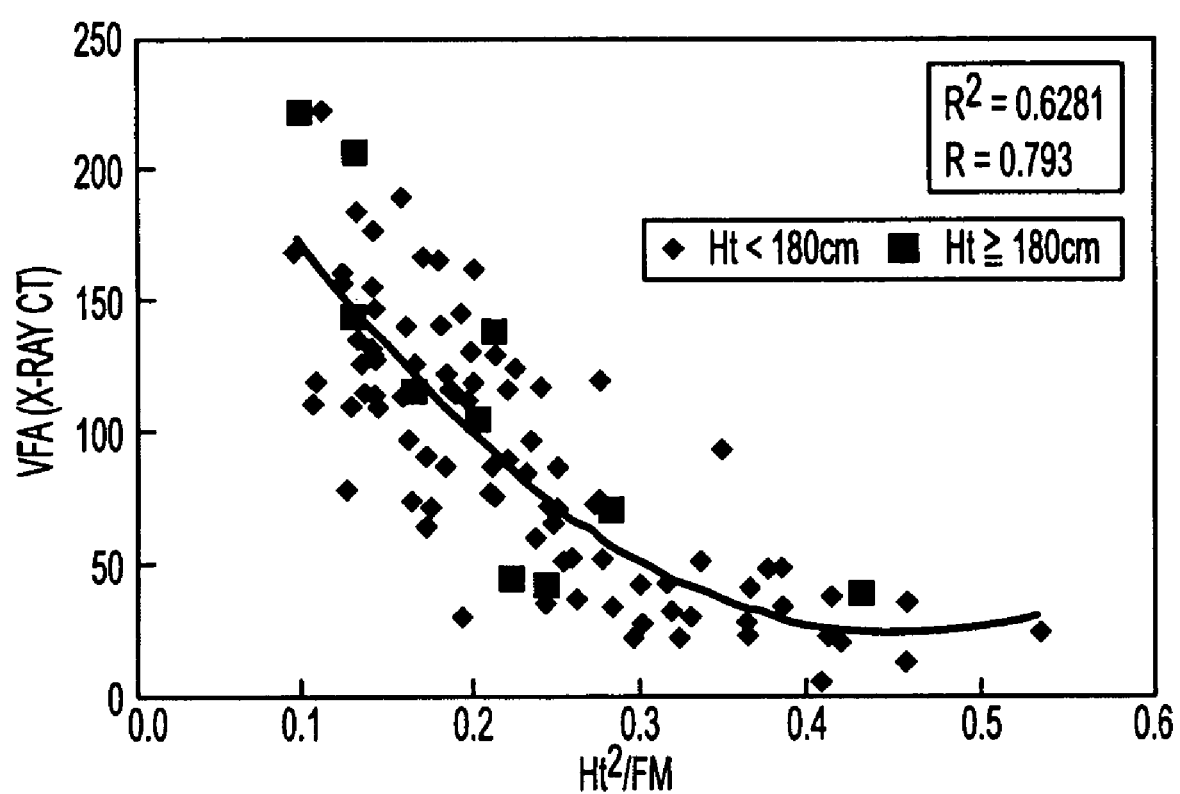
FIG. 2 is a graph showing a correlation between the parameter $Ht^2/FM$ and a visceral fat area measured by X-ray CT.

Also 2 and −1 were determined as alternative applicable numbers for each of X and Y. In this regard, it has also been confirmed as shown in FIG. 2 that the visceral fat area (VFA) correlates closely with a parameter $Ht^2/FM$ (where, X=2 and Y=−1), regardless of height of the subjects. Therefore, estimation of visceral fat area using a parameter expressed as $Ht^2/FM$ is desirable and preferable for decreasing estimating errors due to height.

Further, the present inventors measured a correlation between age (Age) and visceral fat area of a number of subjects, and then performed a multiple regression analysis based on the correlation between age and the visceral fat area and the correlation between the parameter $FM/Ht^2$ and the visceral fat area as shown in FIG. 1. As a result of this effort, an equation (1) as expressed below, where C11, C12 and C13 are each constants C11=6.05 to 22.15 for male or 3.78 to 20.89 for female, C12=0.00 to 4.13 for male or 0.00 to 3.17 for female, and C13=−80.96 to −9.80 for male or −81.57 to −2.72 for female), was sought and determined.

$$VFA = C11*FM/Ht^2 + C12*Age + C13 \qquad (1)$$

Figure 3:
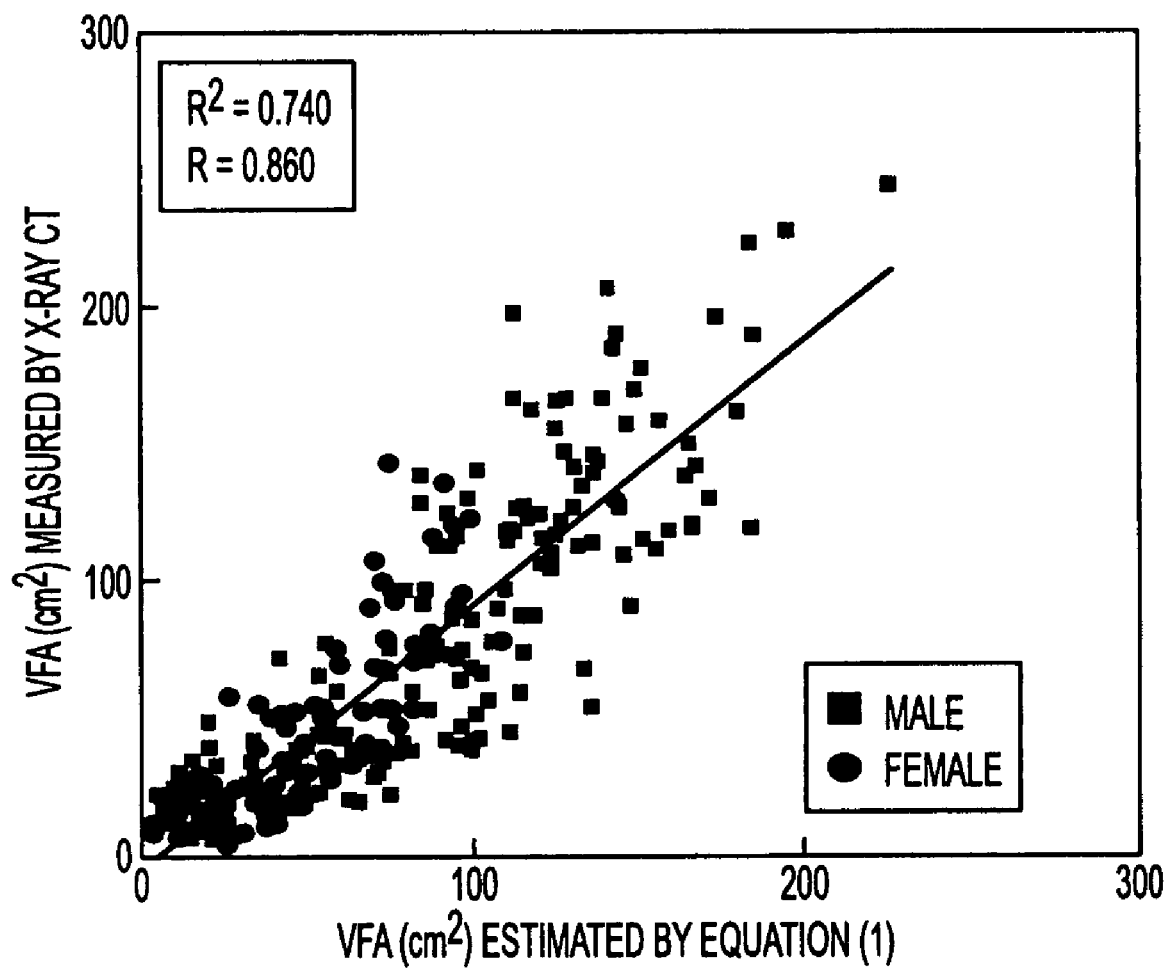
FIG. 3 is a graph showing a correlation between a visceral fat area estimated by the equation (1) and a visceral fat area measured by X-ray CT.

It has been confirmed as shown in FIG. 3 that a visceral fat area estimated by using equation (1) correlates highly with the visceral fat area measured by X-ray CT. Therefore, the estimation of visceral fat area using equation (1) is further desirable and preferable for decreasing estimating errors due to height.

Further, the present inventors performed a multiple regression analysis based on the correlation between age and visceral fat area and the correlation between the parameter $Ht^2/FM$ and the visceral fat area as shown in FIG. 2. As a result of this effort, an equation (2) as expressed below, where C21, C22 and C23 are each constants ($C21=-286.30$ to $-107.80$ for male or $-576.42$ to $-107.80$ for female, $C22=0.00$ to $4.02$ for male or $0.00$ to $4.02$ for female, and $C23=22.00$ to $122.78$ for male or $32.03$ to $122.78$ for female), was sought and determined.

$$VFA=C21*Ht^2/FM+C22*Age+C23 \qquad (2)$$

Figure 4:
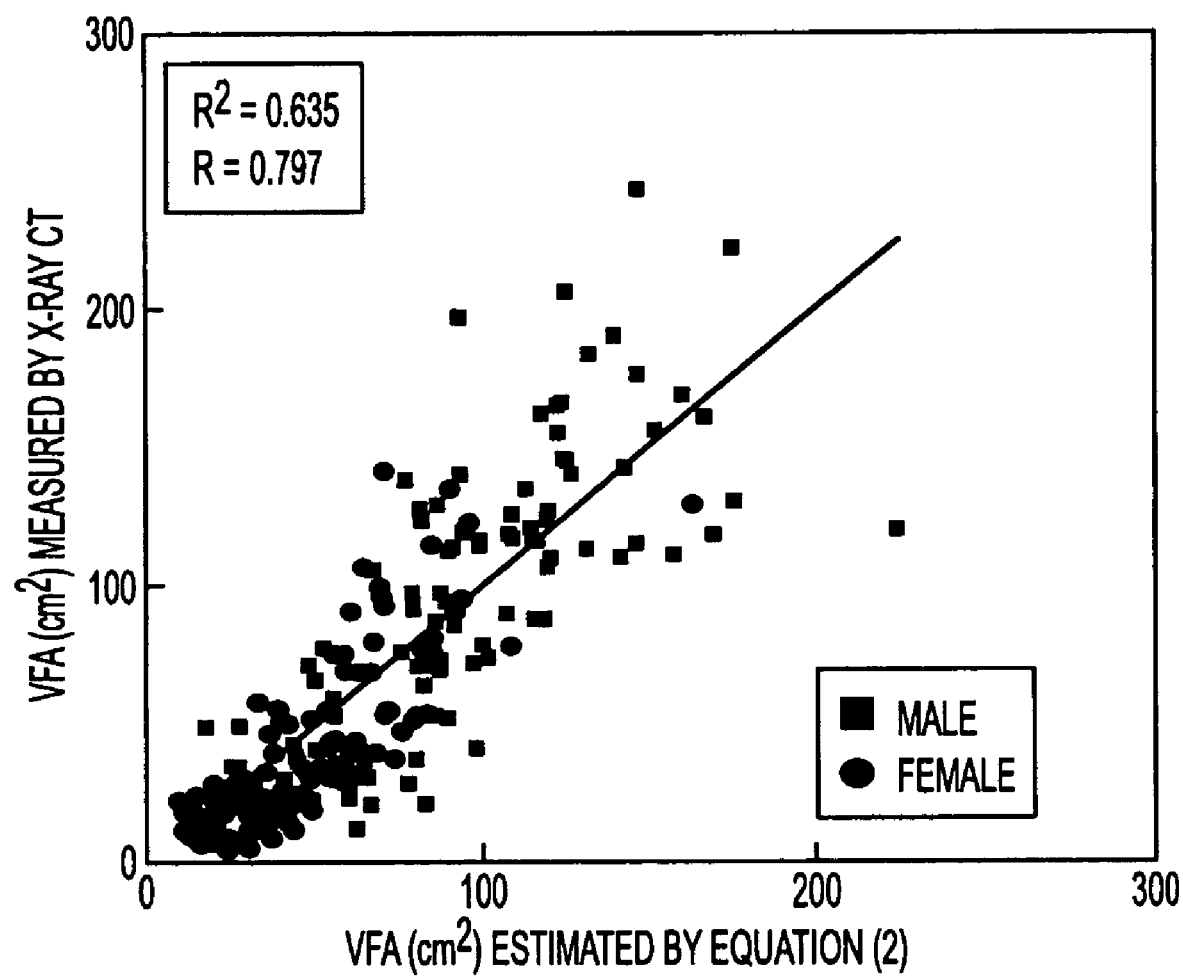
FIG. 4 is a graph showing a correlation between a visceral fat area estimated by the equation (2) and a visceral fat area measured by X-ray CT.

It has been confirmed as shown in FIG. 4 that a visceral fat area estimated using equation (2) correlates highly with visceral fat area measured by X-ray CT. Therefore, estimation of visceral fat area using equation (2) is also desirable and preferable for decreasing estimating errors due to height.

Further, the present inventors measured, in addition to the correlation between age and visceral fat area, a correlation between body mass index, which is well known to be a quotient of weight (Wt) over a square of height ($Ht^2$), and the visceral fat area of a number of subjects, and then performed a multiple regression analysis based on the correlation between age and visceral fat area, the correlation between body mass index ($Wt/Ht^2$) and visceral fat area and the correlation between the parameter $FM/Ht^2$ and visceral fat area as shown in FIG. 1. As a result of this effort, an equation (3) as expressed below, where C31, C32, C33 and C34 are constants ($C31=2.96$ to $20.36$ for male or $-2.91$ to $15.39$ for female, $C32=0.00$ to $4.12$ for male or $0.00$ to $4.45$ for female, $C33=-2.77$ to $7.43$ for male or $-2.77$ to $7.43$ for female, and $C34=-198.40$ to $-8.53$ for male or $-193.90$ to $-7.21$ for female), was determined.

$$VFA=C31*FM/Ht^2+C32*Age+C33*Wt/Ht^2+C34 \qquad (3)$$

Figure 5:
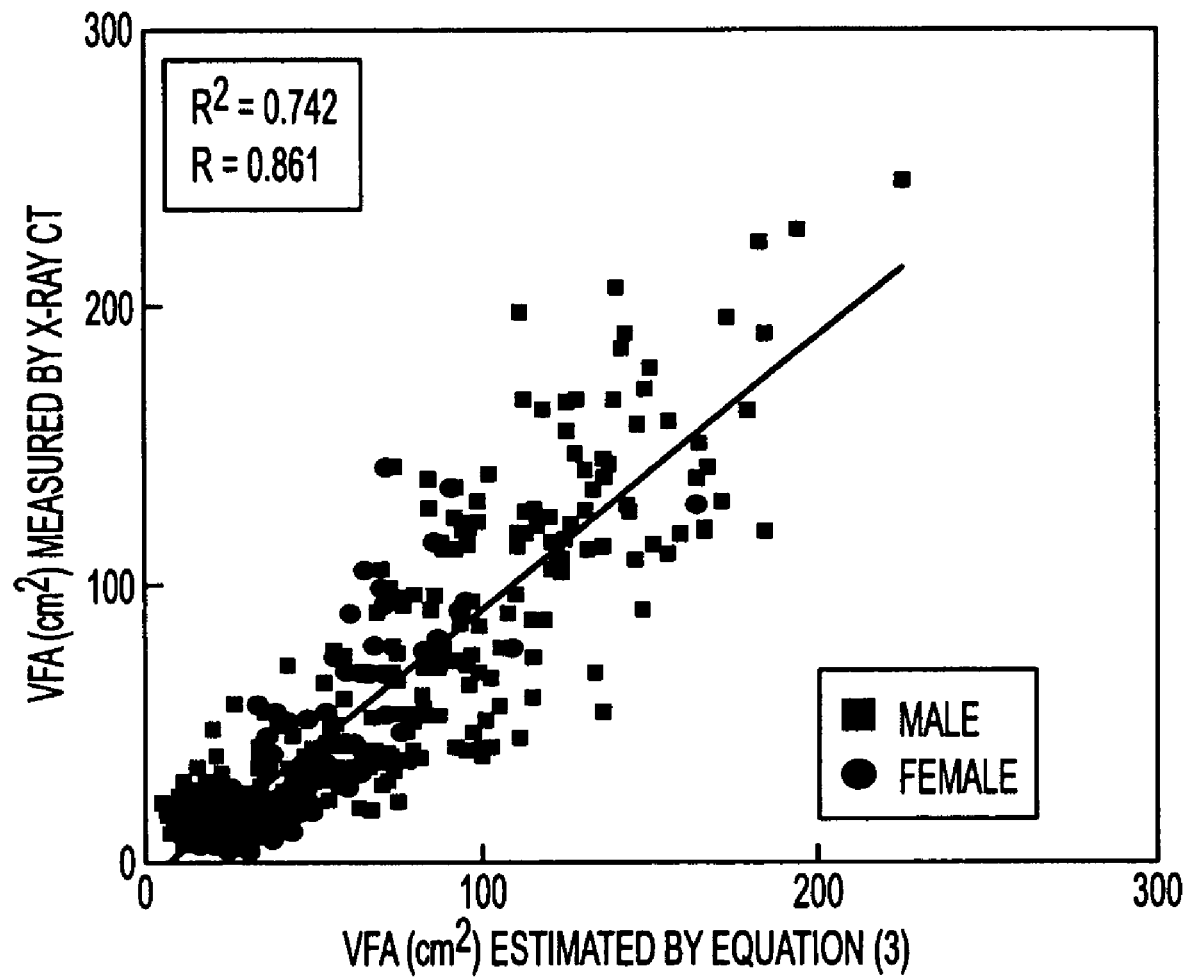
FIG. 5 is a graph showing a correlation between a visceral fat area estimated by the equation (3) and a visceral fat area measured by X-ray CT.

It has been confirmed as shown in FIG. 5 that a visceral fat area estimated by using the equation (3) correlates highly with the visceral fat area measured by X-ray CT. Therefore, estimation of visceral fat area performed using equation (3) is also desirable and preferable for decreasing estimating errors due to height.

Further, the present inventors performed a multiple regression analysis based on the correlation between age and visceral fat area, the correlation between body mass index ($Wt/Ht^2$) and visceral fat area and the correlation between the parameter $Ht^2/FM$ and visceral fat area as shown in FIG. 2. As a result of this effort, an equation (4) as expressed below, where C41, C42, C43 and C44 are constants ($C41=-196.60$ to $-3.88$ for male or $-206.89$ to $61.71$ for female, $C42=0.00$ to $4.05$ for male or $0.00$ to $4.12$ for female, $C43=0.18$ to $16.43$ for male or $0.14$ to $8.11$ for female, and $C44=-205.15$ to $-4.28$ for male or $-198.10$ to $-19.33$ for female), was determined.

$$VFA=C41*Ht^2/FM+C42*Age+C43*Wt/Ht^2+C44 \qquad (4)$$

Figure 6:
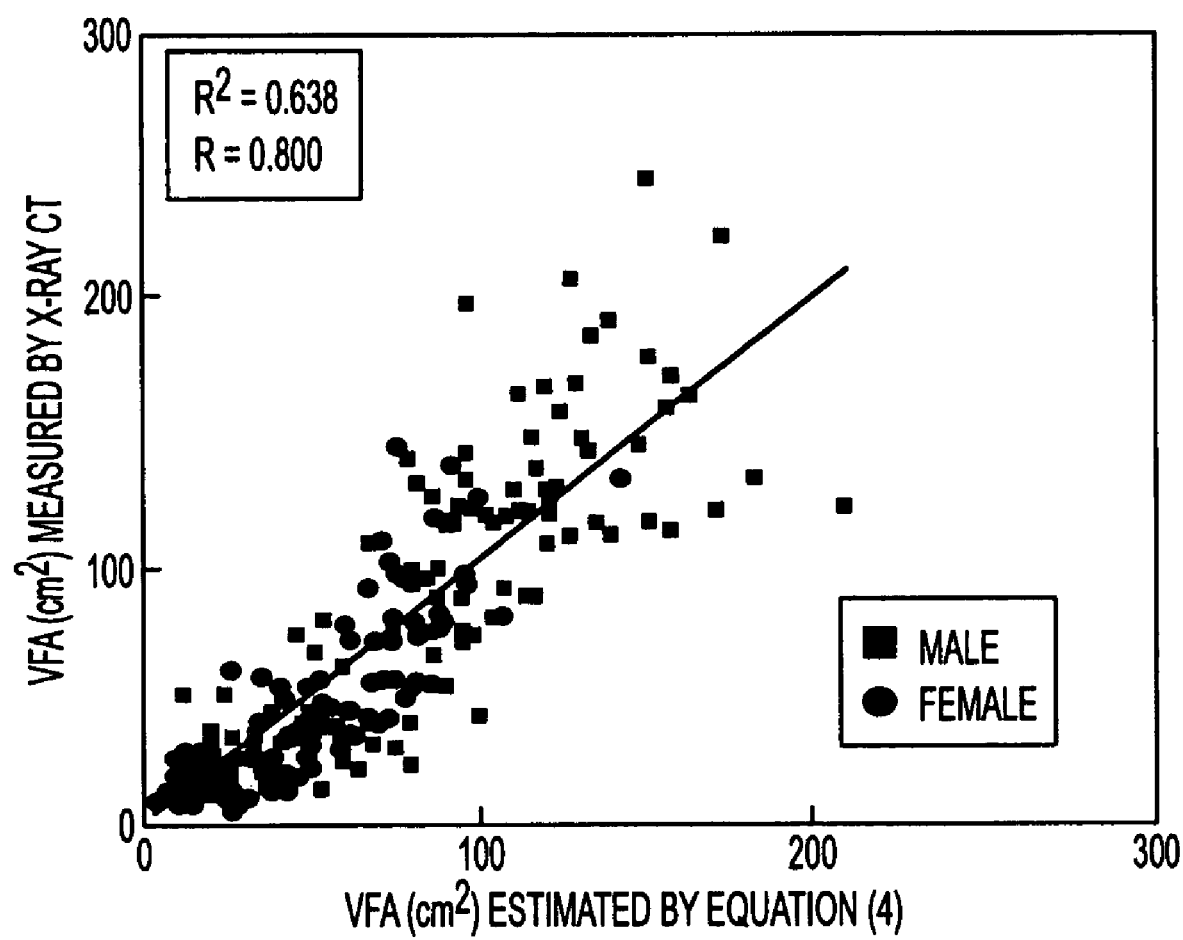
FIG. 6 is a graph showing a correlation between a visceral fat area estimated by the equation (4) and a visceral fat area measured by X-ray CT.

It has been confirmed as shown in FIG. 6 that a visceral fat area estimated by using the equation (4) correlates highly with visceral fat area measured by X-ray CT. Therefore, estimation of visceral fat area performed by using equation (4) is also desirable and preferable for decreasing estimating errors due to height.

Figure 18A:
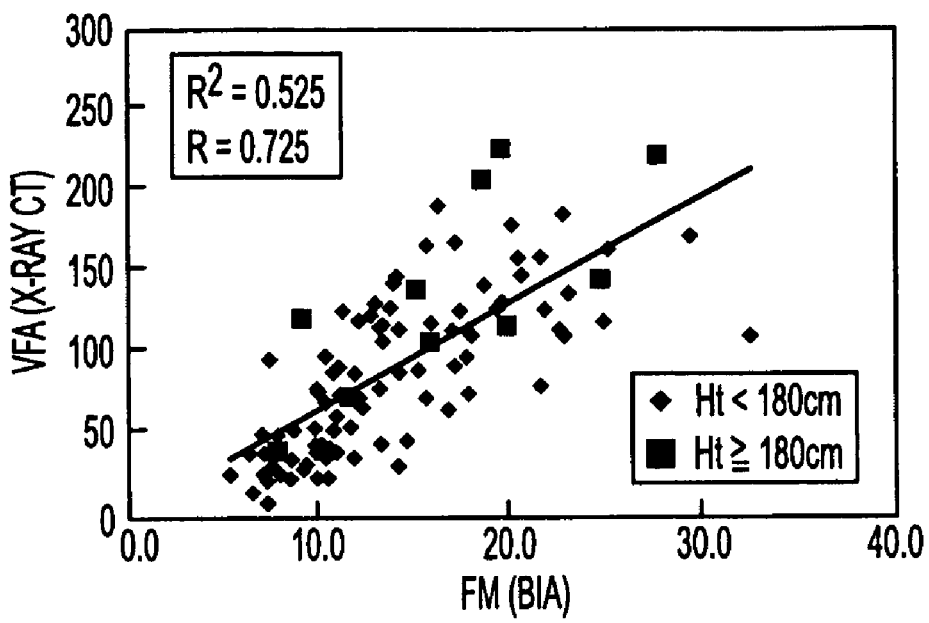
FIG. 18A is a graph showing a correlation between a fat mass measured by BIA and a visceral fat area measured by X-ray CT.
Figure 18B:
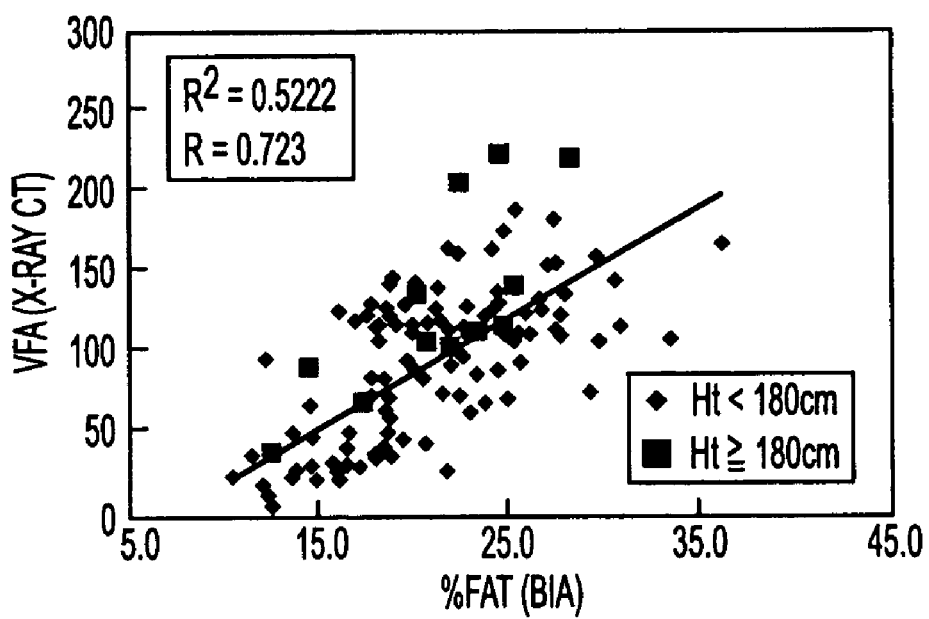
FIG. 18B is a graph showing a correlation between a body fat percentage measured by BIA and a visceral fat area measured by X-ray CT.

Further, the present inventors measured, in addition to the correlation between age and visceral fat area, a correlation between body fat percentage (% FAT) and visceral fat area of a number of subjects (cf. FIG. 18B), and then performed a multiple regression analysis based on the correlation between age and visceral fat area, the correlation between body fat percentage (% FAT) and visceral fat area and the correlation between the parameter $FM/Ht^2$ and visceral fat area as shown in FIG. 1. As a result of this effort, an equation (5) as expressed below, where C51, C52, C53 and C54 are constants ($C51=0.17$ to $32.81$ for male or $-2.15$ to $14.45$ for female, $C52=0.00$ to $4.12$ for male or $0.00$ to $4.12$ for female, $C53=-5.03$ to $8.80$ for male or $0.00$ to $5.13$ for female, and $C54=-121.25$ to $-5.74$ for male or $-104.24$ to $-7.43$ for female), was determined.

$$VFA=C51*FM/Ht^2+C52*Age+C53*\% FAT+C54 \qquad (5)$$

Figure 7:
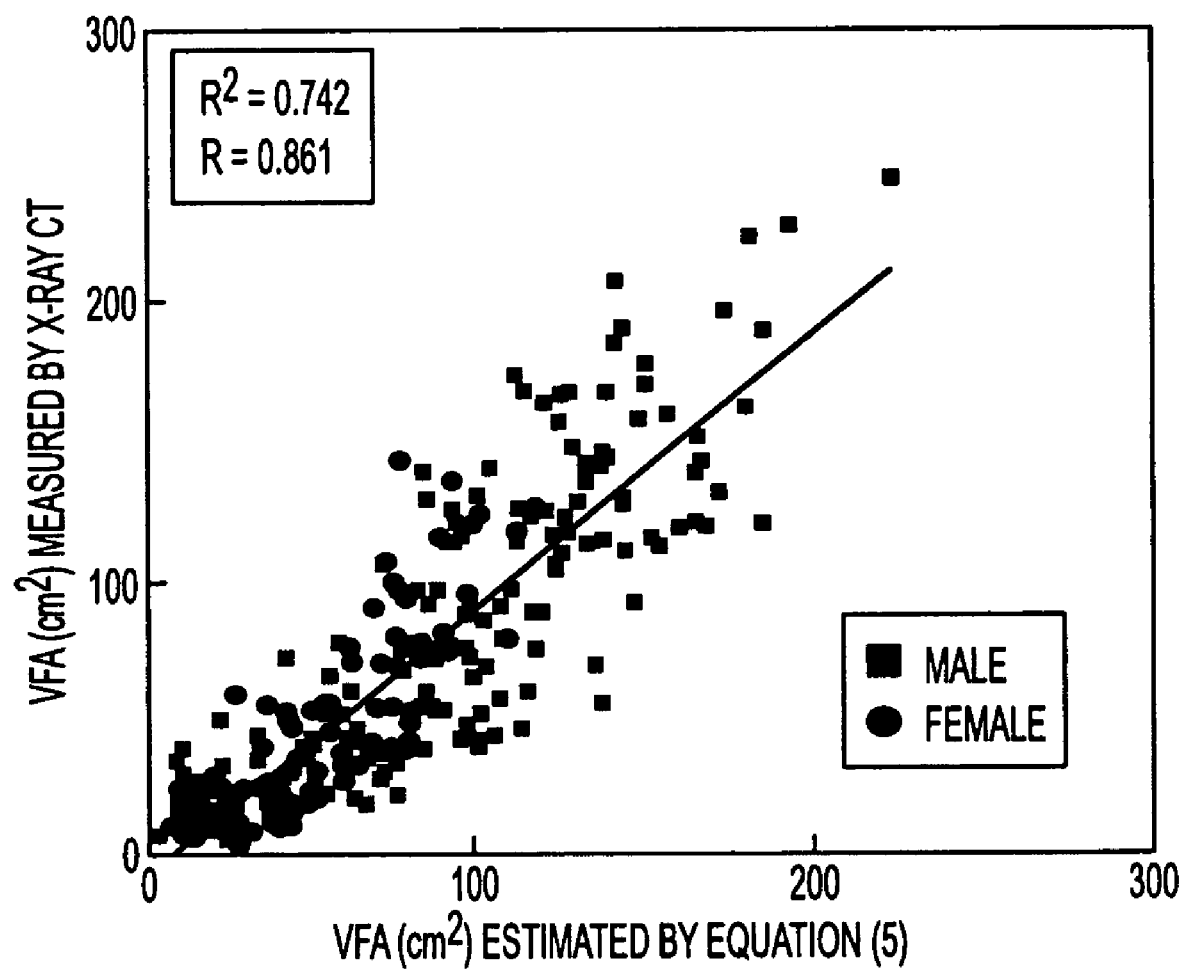
FIG. 7 is a graph showing a correlation between a visceral fat area estimated by the equation (5) and a visceral fat area measured by X-ray CT.

It has been confirmed as shown in FIG. 7 that a visceral fat area estimated by using equation (5) correlates highly with visceral fat area measured by X-ray CT. Therefore, estimation of visceral fat area performed by using equation (5) is also desirable and preferable for decreasing estimating errors due to height.

Further, the present inventors performed a multiple regression analysis based on the correlation between age and visceral fat area, the correlation between body fat percentage (% FAT) and visceral fat area and the correlation between the parameter $Ht^2/FM$ and visceral fat area as shown in FIG. 2. As a result of this effort, an equation (6) as expressed below, where C61, C62, C63 and C64 are constants ($C61=-107.96$ to $154.97$ for male or $-216.05$ to $139.62$ for female, $C62=0.00$ to $4.10$ for male or $0.00$ to $2.08$ for female, $C63=1.00$ to $14.15$ for male or $0.08$ to $15.14$ for female, and $C64=-197.01$ to $-5.91$ for male or $-184.11$ to $-1.60$ for female), was determined.

$$VFA=C61*Ht^2/FM+C62*Age+C63*Wt/Ht^2+C64 \qquad (6)$$

Figure 8:
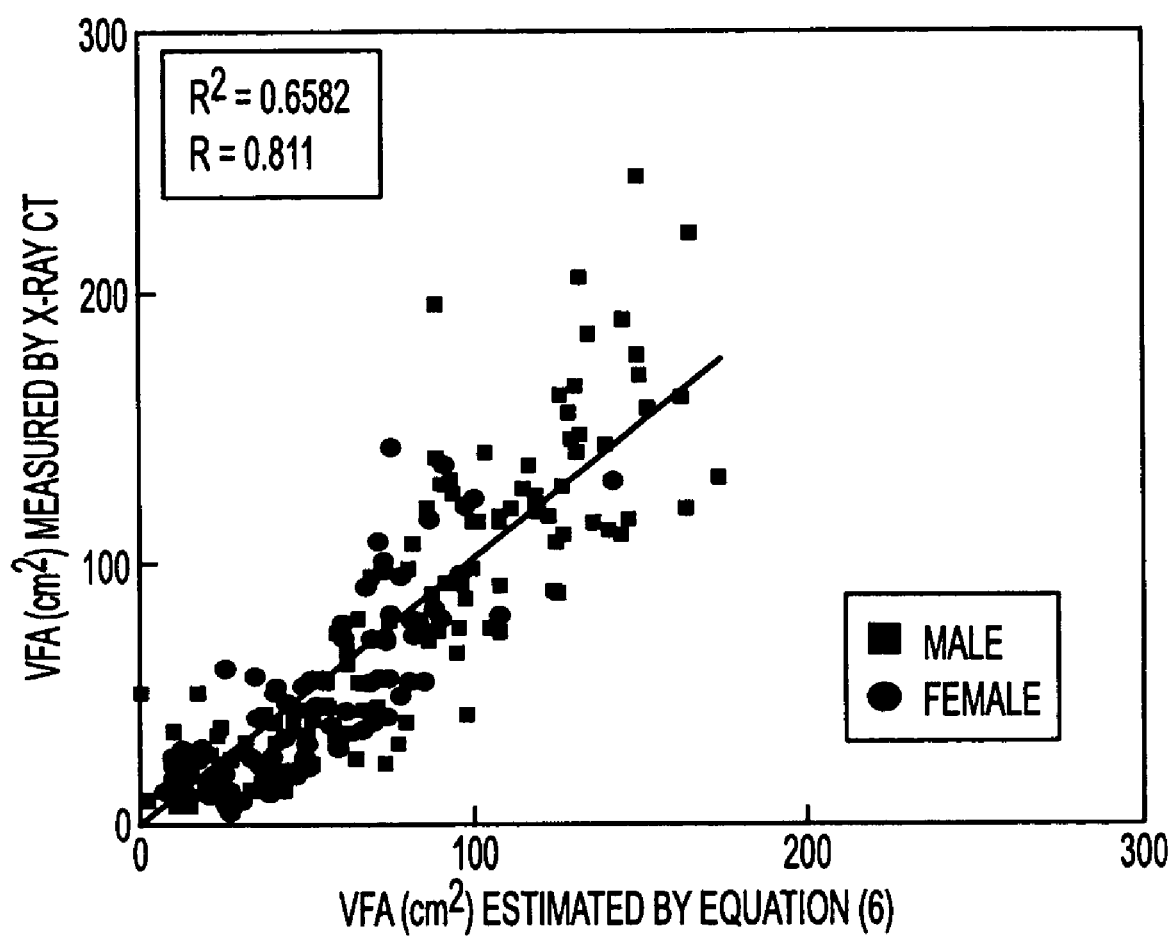
FIG. 8 is a graph showing a correlation between a visceral fat area estimated by the equation (6) and a visceral fat area measured by X-ray CT.

It has been confirmed as shown in FIG. 8 that a visceral fat area estimated by using equation (6) correlates highly with visceral fat area measured by X-ray CT. Therefore, estimation of visceral fat area performed using equation (6) is also desirable and preferable for decreasing estimating errors due to height.

In and for the methods according to the present invention, BIA is recommended as a simple and accurate technique for acquiring the fat mass of a subject. Also, other techniques can be used, including, for example, Under Water Weighing, Dual Energy X-ray Absorptiometry, or Infrared Interactance. Other well-known techniques for estimating fat mass based on body mass index or based on subcutaneous fat measurement using a caliper or ultrasound can also be used when practicing the present invention.

It is also known that the above constants C11 to C64 vary according to personal parameters including intensity of daily activity (the so called "Physical Activity Level"), presence or absence of menstruation, age at the onset of menopause and/or the number of years elapsed after the onset of menopause, etc. Therefore, when the constants are adjusted or calibrated in accordance with such personal parameters, visceral fat area can probably be estimated more accurately.

(Embodiment 1)

Next, a system for estimating a visceral fat area according to an embodiment of the present invention as described above will be described.

Figure 9:
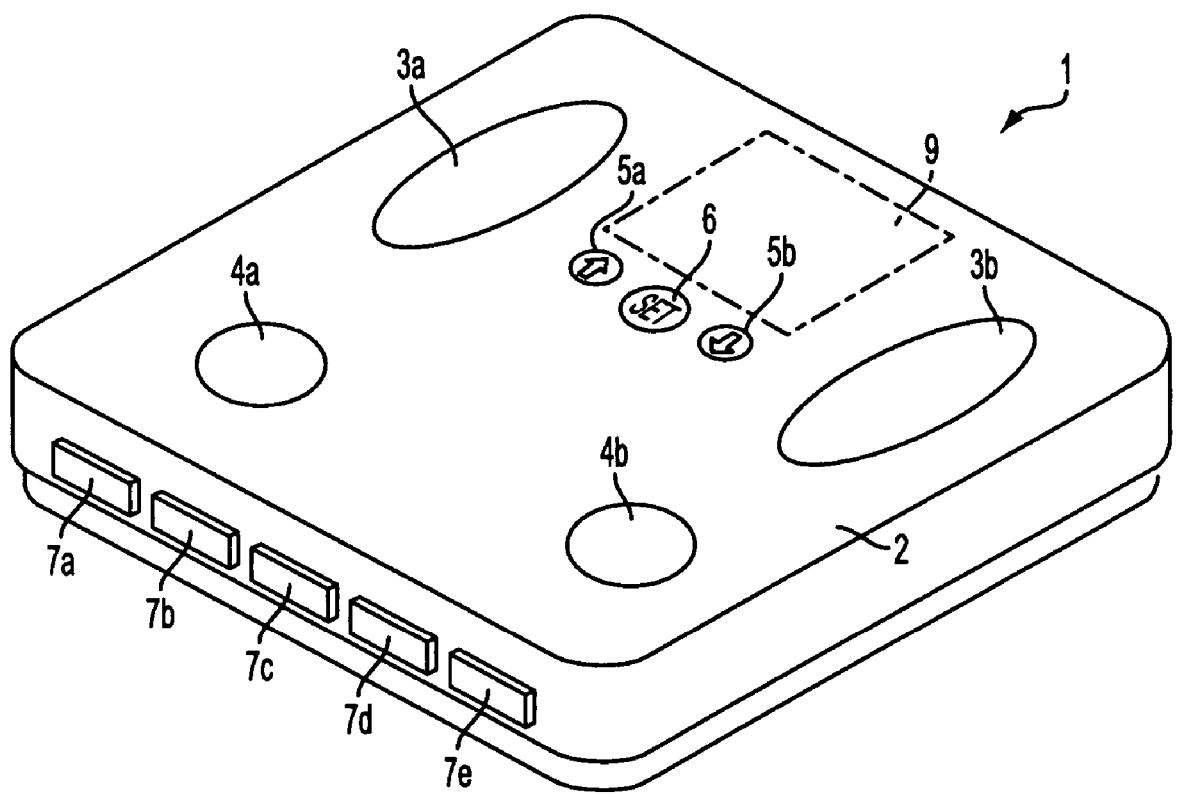
FIG. 9 is a schematic view showing an external appearance of a visceral fat area estimating system as one embodiment of the present invention.
Figure 10:
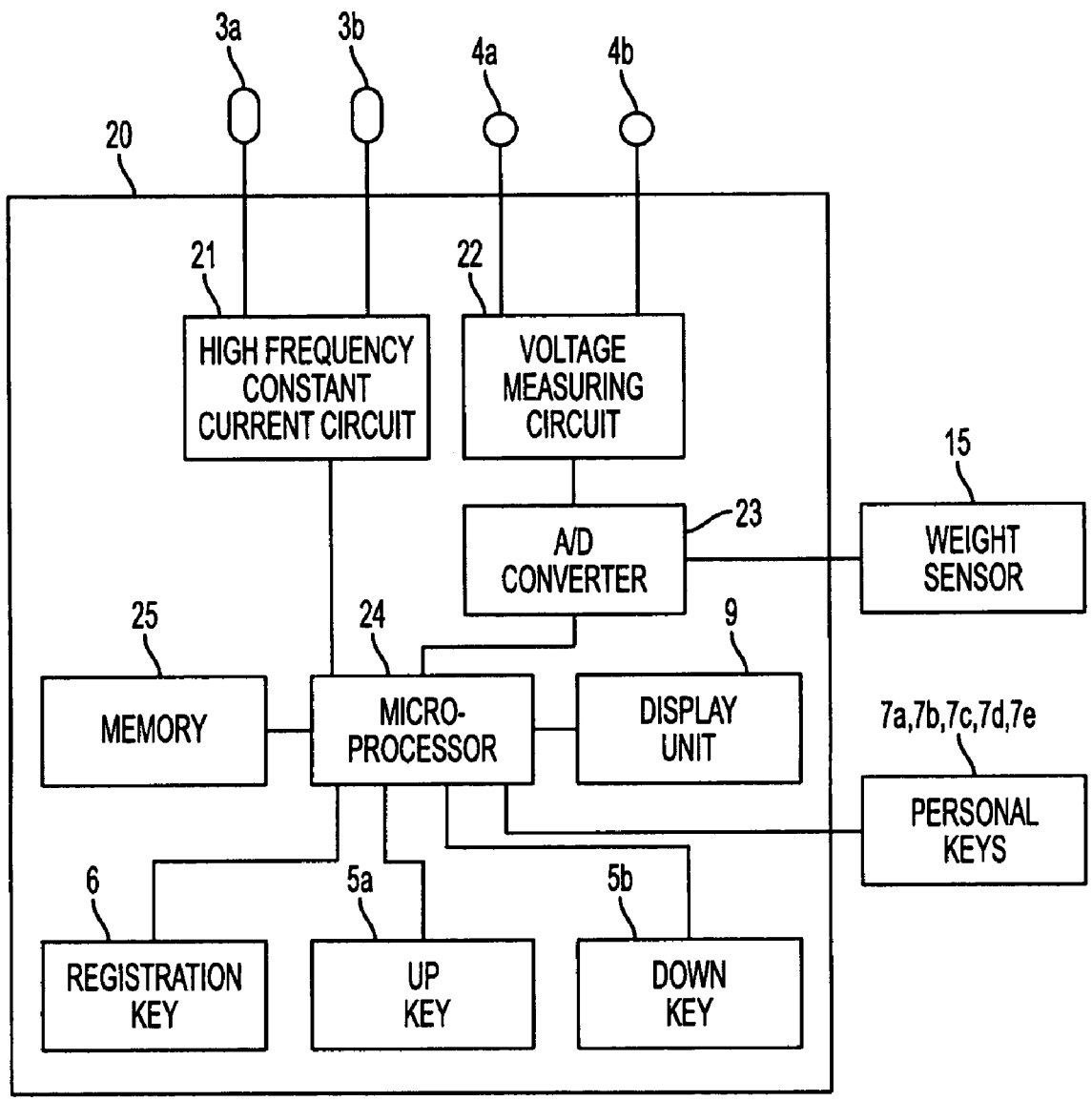
FIG. 10 is a block diagram showing an electric circuit arrangement of the system of FIG. 9.

FIG. 9 is a schematic view showing the external appearance of a visceral fat area estimating system. FIG. 10 is a block diagram showing an electric circuit arrangement of the system of FIG. 9. An estimating system 1 of the present embodiment has, on a weighing platform 2 of a scale, current-carrying electrodes 3a and 3b for forming a current path in a living body, measuring electrodes 4a and 4b for detecting a potential difference which occurs in the living body, a setting key 6 for setting personal data including a height, age and gender as well as time, an UP key 5a for incrementing a numerical value, a DOWN key 5b for decrementing a numerical value, personal keys 7a to 7e for making a measurement based on retrieved personal data, and a display unit 9 for displaying the status of set conditions, results of measurements or results of determinations. Further, as shown in FIG. 10, inside platform 2, a weight sensor 15 for detecting a load and converting it into an electric signal, an electronic circuit board 20 and the like are provided. The personal keys 7a to 7e and setting key 6 also serve as a power switch. Upon pressing any one of personal keys 7a to 7e or setting key 6, the system is activated. The system is deactivated after passage of a certain period of time after the results of measurement are is displayed or even during entry of data.

The electronic circuit board 20 has the display unit 9 on platform 2, the setting key 6, the UP key 5a, the DOWN key 5b, a high frequency low current circuit 21 for applying a very weak constant current of high frequency to the current-carrying electrodes 3a and 3b, a voltage measuring circuit 22 for measuring a potential difference in a living body which occurs between the measuring electrodes 4a and 4b, an A/D conversion circuit 23 for converting an analog signal from the voltage measuring circuit 22 or weight sensor 15 into a digital signal, a memory 25 for storing set and registered conditions, measured data and the like, and a microprocessor 24 for computing a percent body fat and the like based on measurement conditions, measured bioelectrical impedance data and body weight data and controlling. The electronic circuit board 20 is connected to each of the current-carrying electrodes 3a and 3b, measuring electrodes 4a and 4b, weight sensor 15 and personal keys 7a, 7b, 7c and 7d via electric wiring.

Figure 11:
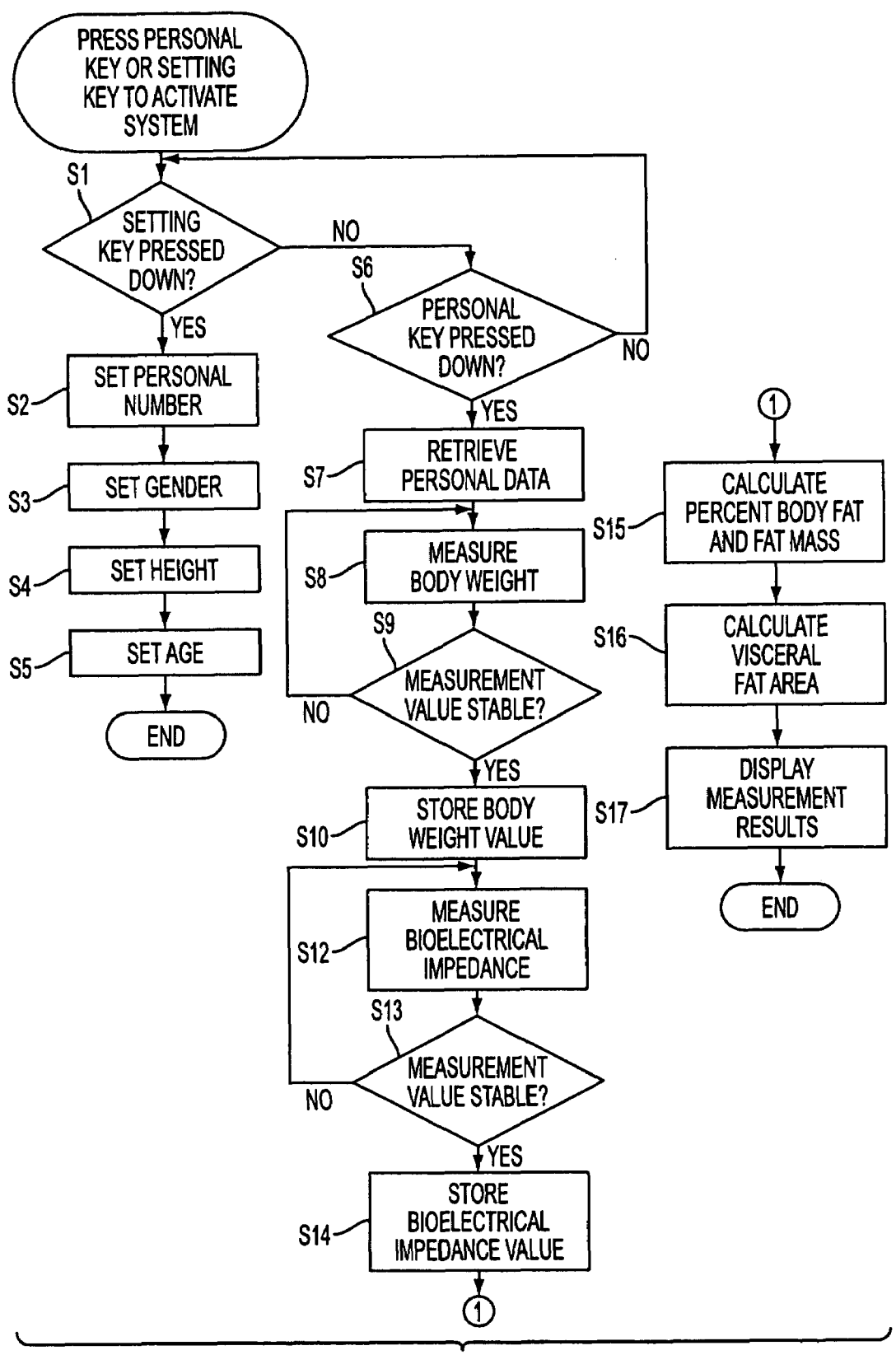
FIG. 11 is a flowchart illustrating steps to be performed by the system of FIG. 9.

FIG. 11 is a flowchart illustrating steps for estimating a visceral fat area to be performed by the visceral fat area estimating system of the present embodiment. Hereinafter, overall operation will be described with reference to the flowchart. STEPS S2 to S5 will be described briefly since these are in the prior art. Upon pressing of any one of the personal keys 7a to 7e or the setting key 6, the system is activated. When the setting key 6 is pressed down, settings of personal data including a height, age and gender can be made. When one of the personal keys is pressed down, personal data set by means of the setting key is read from the memory 25, and a measurement is made based on the data. In STEP S1, it is determined whether the setting key 6 has been pressed down. If a key other than the setting key 6 has been pressed down, the system proceeds to STEP S6. In STEP S2, a personal number to be set is entered. On the display unit 9, a personal number "1" is displayed. Each time the UP key 5a is pressed, the personal number is incremented by 1. Meanwhile, each time the DOWN key 5b is pressed, the personal number is decremented by 1. Upon pressing of the setting key 6, the personal number is set and then stored in the memory 25. In STEP S3, gender is entered and set in the same manner as the personal number. In STEP S4, a height is set. In this STEP, since an initial value of the height is displayed on the display unit 9, the height value can be incremented and decremented by use of the UP key 5a and the DOWN key 5b, respectively. When the value reaches a desired value, the height value is confirmed by press of the setting key 6. In STEP S5, age is set in the same manner as the height. Then, the program is terminated.

In STEP S6, if none of the personal keys 7a to 7e has been pressed down, the system returns to STEP S1. In STEP S7, personal data such as gender and a height which corresponds to a pressed personal key is read from the memory 25 and displayed on the display unit 9 to encourage an subject to check whether he has pressed down the right personal key.

In STEP S8, when the subject stands on the platform 2, his body weight is measured. In STEP S9, if a stable measurement value cannot be obtained, the system returns to STEP S8. In STEP S10, the weight value is stored in the memory 25.

In STEP S12, a bioelectrical impedance is measured in the following manner. The high frequency constant current circuit 21 outputs a very weak constant current I of high frequency. This output current is applied to the subject via the current-carrying electrodes 3a and 3b. At this time, the current passing through the subject is detected by the voltage measuring circuit 22 as a potential difference in the living body which occurs between the measuring electrodes 4a and 4b. This analog output is converted to a digital signal V by the A/D converter 23. A bioelectrical impedance Z is determined by an equation Z=V/I. In STEP S13, if a stable measurement value cannot be obtained, the system returns to STEP S12. In STEP S14, the measured bioelectrical impedance value is stored in the memory 25.

Then, the system proceeds to STEP S15 in which a percent body fat is calculated from the body weight, the height and the bioelectrical impedance value measured in STEP S12. Description of a method for calculating the percent body fat will be omitted since it is known to those skilled in the art. To determine a fat mass, the body weight is multiplied by the percent body fat.

In STEP S16, a visceral fat area is estimated by using the equation (1). However, any of equations (2) to (6) mentioned above can be used instead of equation (1).

In STEP S17, as shown in FIG. 12, the measurement values and the values calculated from the measurement values are displayed on the display unit 9.

In the above embodiment, a scale and a body fat meter are provided. However, in the case of a body fat meter such as a card-type body fat meter which is equipped with no scale, a body weight value can be entered manually by use of the UP key 5a, the DOWN key 5b and the setting key 6. In this case, average body weight values of a male and a female are stored in the memory in advance, and the numeric value is incremented or decremented by means of the UP key 5a and the DOWN key 5b and confirmed as a body weight of the subject by means of the setting key 6. Further, in the case of an ordinary calculator which is not equipped with a percent body fat meter, a percent body fat can be entered manually as in the case of the body weight value. As for a height value, although it is entered manually by means of the keys in the above embodiment, a height measuring device may be used to obtain the value.

According to the definition of a percent body fat, a fat mass can be determined once a body, weight and the percent body fat are determined. Therefore, if a conventional scale equipped with a body fat meter is available, all input variables of the equation (1) for estimating a visceral fat area can be determined, and a visceral fat area can be estimated by the estimation method of the present invention.

In the estimating system 1 of the above embodiment, a bioelectrical impedance between the subject's feet has been measured. However, the present invention is not limited to this, and a bioelectrical impedance between hands or between a hand and a foot may be measured instead.

(Embodiment 2)

Figure 13A:
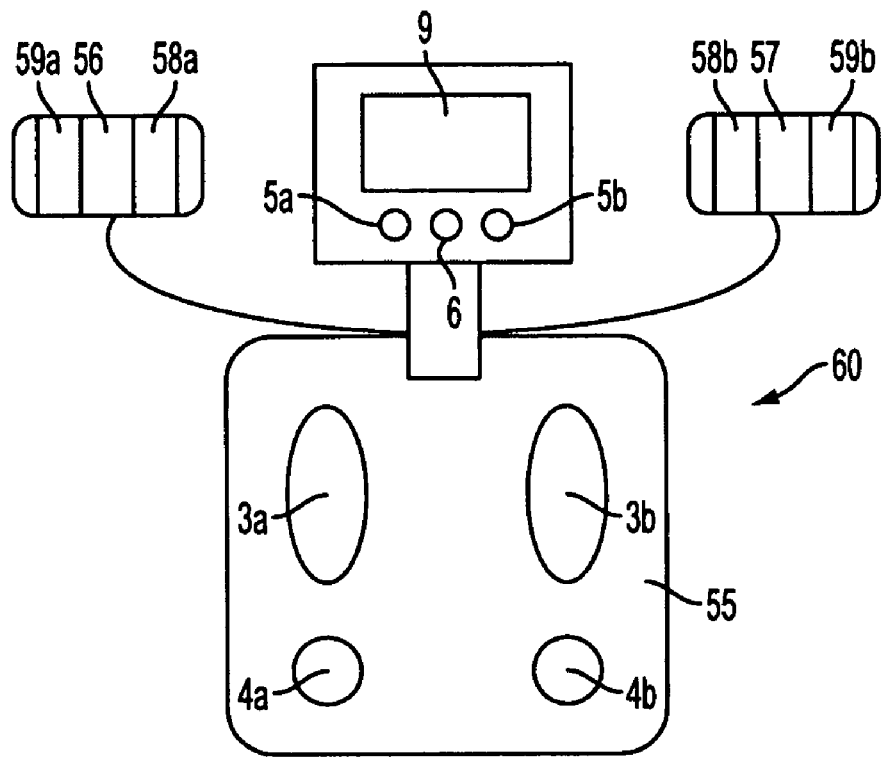
FIG. 13A is a schematic view showing an external appearance of a visceral fat area estimating system of another embodiment of the present invention.
Figure 13B:
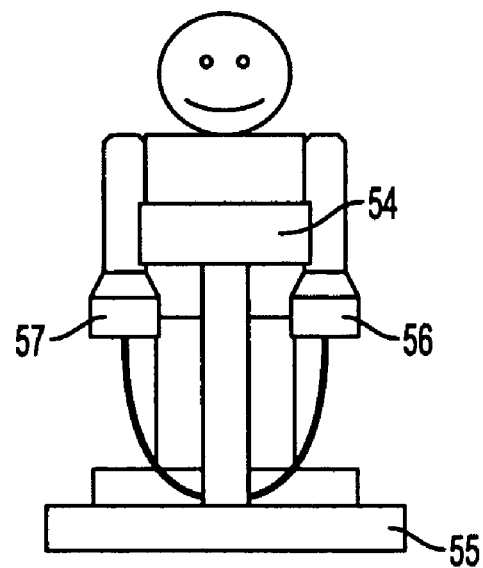
FIG. 13B is a schematic view showing a use of the system of FIG. 13A.

Next, another embodiment of the present invention will be described. FIG. 13A is a schematic view showing an external configuration of a second embodiment of the visceral fat estimating system according to the present invention, and FIG. 13B is a schematic view showing a use thereof. An estimating system 60 of the present embodiment is different from the first embodiment shown in FIG. 9 in that electrodes 56 and 57 for hands are additionally provided. The same constituents as those in the first embodiment are given the same reference numerals as those given to the constituents in the first embodiment. Electrode 56 for the left hand comprises a constant current applying electrode 58a and a voltage measuring electrode 59a. Similarly, electrode 57 for the right hand comprises a constant current applying electrode 58b and a voltage measuring electrode 59b.

Figure 14:
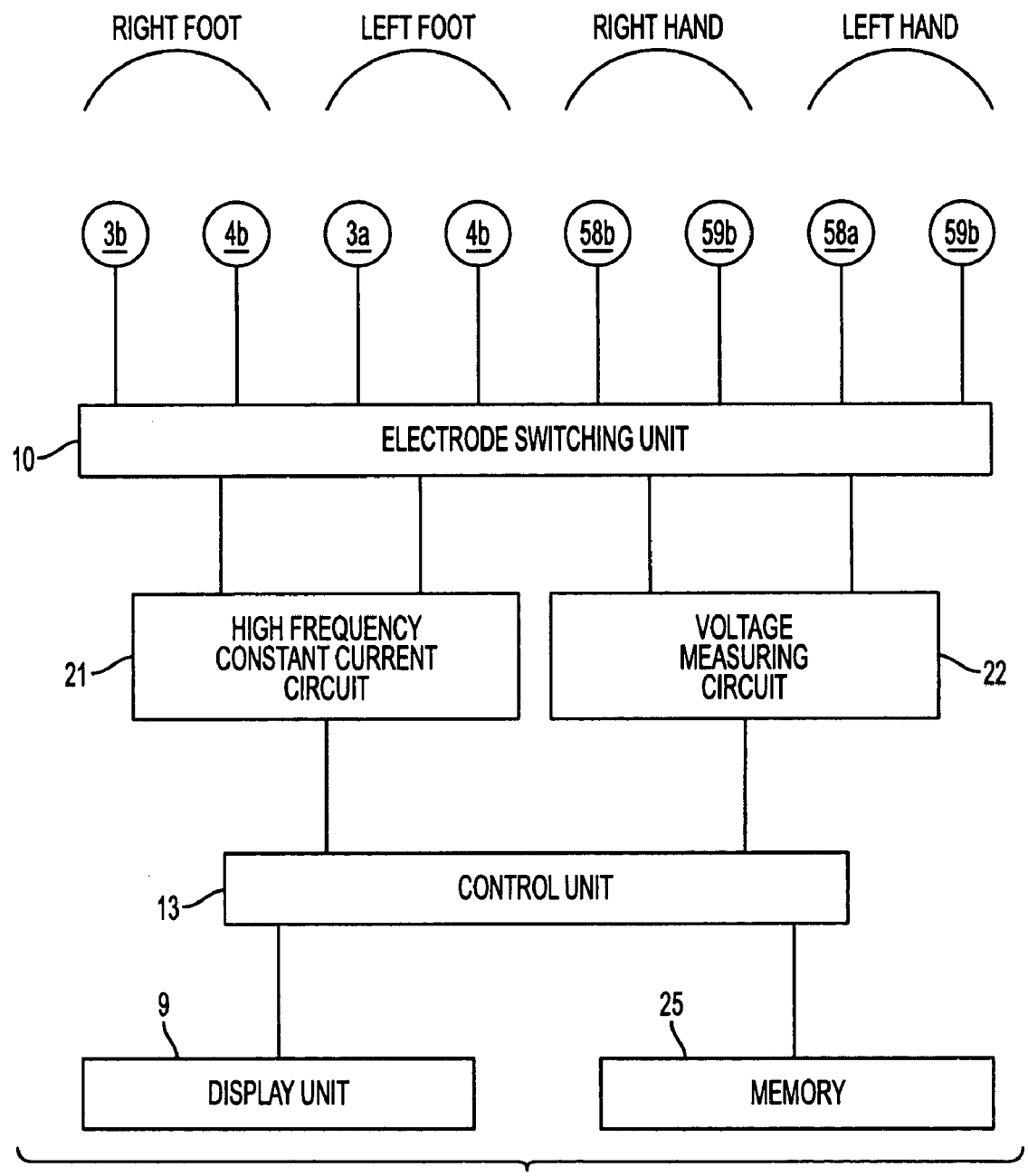
FIG. 14 is a block diagram showing an electric circuit arrangement of the system of FIG. 13A.

FIG. 14 is an electric block diagram of the estimating system 60 of the present embodiment. Eight electrodes which contact both hands and feet, i.e., electrodes 3a, 3b, 4a, 4b, 58a, 58b, 59a and 59b, are connected to an electrode switching unit 10. The electrode switching unit 10 is connected to a control unit 13 via the high frequency constant current circuit 21 and the voltage measuring circuit 22. The control unit 13 includes a microcomputer and is connected to a memory 25 for storing a variety of data.

Figure 15:
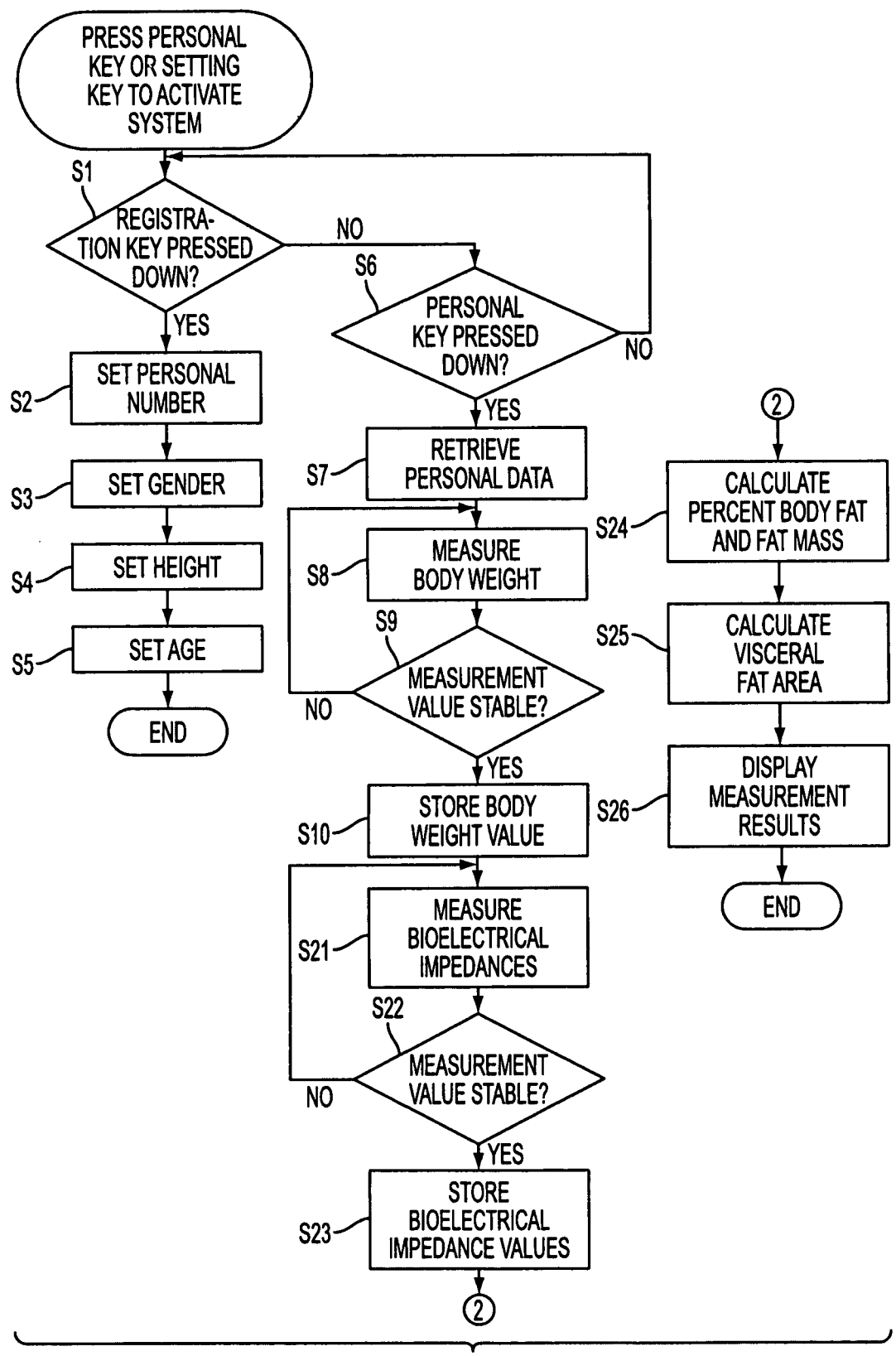
FIG. 15 is a flowchart illustrating steps to be performed by the system of FIG. 13A.

Next, operations of the estimating system 60 of the present embodiment will be described with reference to a flowchart in FIG. 15. Steps for the same operations as those of steps shown in FIG. 11 are given the same step numbers as those given to the steps of FIG. 11. Descriptions of STEPS S1 to S10 will be omitted since they are the same as STEPS S1 to S10 in FIG. 11.

In STEP S21, the switching unit 10 is switched according to a direction from the control unit 13, whereby an alternating current is supplied from the high frequency constant current circuit 21 to the electrodes 3a and 3b, and voltages are measured at the electrodes 4a and 4b by the voltage measuring circuit 22. Then, the control unit 13 calculates a bioelectrical impedance (BI) from the measured voltages. Thus, BI is measured for a whole body and each of the following body parts, i.e., the right foot, the left foot, the right hand and the left hand. In STEP S22, if a stable measurement value cannot be obtained, the system returns to STEP S21. In STEP S23, the measured BI values are stored in the memory 25.

In STEP S24, percent body fats and fat masses are calculated from the measured BIs. Firstly, a percent body fat and fat mass of the whole body are calculated from the BI of the whole body. Subsequently, a percent body fat, fat free mass and fat mass of each of the right foot, the left foot, the right hand and the left hand are calculated from the BI of each of the right foot, the left foot, the right hand and the left hand, respectively. Then, a total of the fat masses of the body parts is calculated. Thereafter, the total of the fat masses of the body parts is subtracted from the fat mass of the whole body so as to determine a fat mass of a trunk.

In STEP S25, a visceral fat area is estimated by using equation (1). As the fat mass FM in the equation, the fat mass of the trunk is used. Any of equations (2) to (6) mentioned above can be used instead of equation (1).

Figure 17:
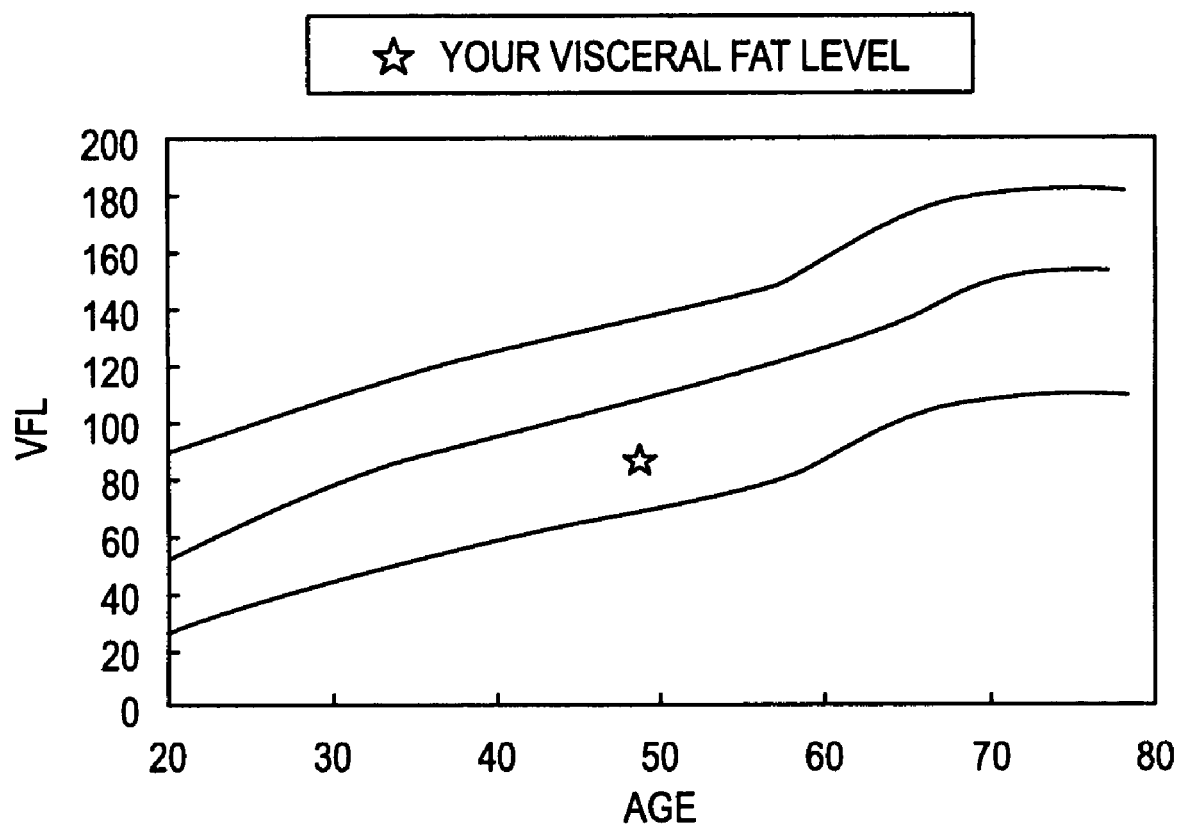
FIG. 17 is another example of a display of the system of FIG. 13A.

In STEP S26, as shown in FIG. 16 and FIG. 17, the measurement values and the values calculated from the measurement values are displayed on the display unit 9. In particular, FIG. 17 shows an example displaying a visceral fat level that is a value indicating a degree of accumulation of visceral fat. The visceral fat level of a user which is also estimated by using equation (1), or any of equations (2) to (6) as the case may be, is plotted as a star on a graph area using the vertical axis for the visceral fat level (VFL) and the horizontal axis for age (AGE). For the purpose of enabling a user to easily recognize his/her visceral fat level, a standard (average) line indicating a standard visceral fat level estimated from a number of subjects is displayed on the graph area with and between its relevant lines which indicate, for example, the standard deviations or the maximum and minimum data.

As described above, in the method according to the present invention, estimation of a value indicating visceral fat area is performed by using the product of an Xth power of the height value and a Yth power of the fat mass value, preferably by using the parameter expressed as $FM/Ht^2$ or $Ht^2/FM$, more preferably by using one of equations (1) to (6). This method for estimating visceral fat area has the potential to decrease estimation errors due to height, and enables anyone to estimate visceral fat area securely without concern for exposure to X-rays, at low costs, and with proper accuracy.

In the system according to the present invention, the data processing unit estimates the value indicating visceral fat area by using the product of an Xth power of the height value and a Yth power of the fat mass value, preferably by using the parameter expressed as $FM/Ht^2$ or $Ht^2/FM$, more preferably by using one of the equations (1) to (6). This system for estimating visceral fat area has the potential to decrease estimation errors due to height, and enables any to estimate visceral fat area securely without concern for exposure to X-rays, at low costs, and with proper accuracy.

Therefore, the present method and system for estimating visceral fat area can be used for tall subjects as well as short subjects, thereby enabling common use by a number of nations each having a different average height and consequently enabling decrease in cost of development and manufacturing.

What is claimed is:

1. A method for estimating visceral fat area of a subject, comprising the steps of:
    acquiring predetermined biological data of the subject including at least values indicating height and fat mass of the subject, and
    estimating a value indicating visceral fat area of the subject based on the acquired biological data,
    wherein the estimation of the value indicating visceral fat area is performed by using a parameter expressed as $Ht^2/FM$, where Ht is the value indicating height and FM is the value indicating fat mass.

2. The method of claim 1, wherein a value indicating age of the subject is further acquired in the step of acquiring the biological data and wherein the estimation of the value indicating visceral fat area is performed by using an equation (2) as follows:

$$VFA = C21*Ht^2/FM + C22*Age + C23 \quad (2)$$

where VFA is the value indicating visceral fat mass, Age is the value indicating age, and C21, C22 and C23 are constants.

3. The method of claim 1, wherein values indicating age and weight of the subject are further acquired in the step of acquiring the biological data and wherein the estimation of the value indicating visceral fat area is performed by using an equation (4) as follows:

$$VFA = C41*Ht^2/FM + C42*Age + C43*Wt/Ht^2 + C44 \quad (4)$$

where VFA is the value indicating visceral fat mass, Age is the value indicating age, Wt is the value indicating weight, and C41, C42, C43 and C44 as constants.

4. The method of claim 1, wherein values indicating age and body fat percentage of the subject are further acquired in the step of acquiring the biological data and wherein the estimation of the value indicating visceral fat area is performed by using an equation (6) as follows:

$$VFA = C61*Ht^2/FM + C62*Age + C63* \% FAT + C64 \quad (6)$$

where VFA is the value indicating visceral fat mass, Age is the value indicating age, % FAT is the value indicating body fat percentage, and C61, C62, C63 and C64 are constants.

5. A method for estimating visceral fat area of a subject, comprising the steps of:
acquiring predetermined biological data of the subject including at least values indicating height and fat mass of the subject, and
estimating a value indicating visceral fat area of the subject based on the acquired biological data,
wherein a value indicating age of the subject is further acquired in the step of acquiring the biological data and wherein the estimation of the value indicating visceral fat area is performed by using an equation (1) as follows:

$$VFA = C11*FM/Ht^2 + C12*Age + C13 \quad (1)$$

where Ht is the value indicating height, FM is the value indicating fat mass, VFA is the value indicating visceral fat mass, Age is the value indicating age, and C11, C12 and C13 are constants.

6. A method for estimating visceral fat area of a subject, comprising the steps of:
acquiring predetermined biological data of the subject including at least values indicating height and fat mass of the subject, and
estimating a value indicating visceral fat area of the subject based on the acquired biological data,
wherein values indicating age and weight of the subject are further acquired in the step of acquiring the biological data and wherein the estimation of the value indicating visceral fat area is performed by using an equation (3) as follows:

$$VFA = C31*FM/Ht^2 + C32*Age + C33*Wt/Ht^2 + C34 \quad (3)$$

where Ht is the value indicating height, FM is the value indicating fat mass, VFA is the value indicating visceral fat mass, Age is the value indicating age, Wt is the value indicating weight, and C31, C32, C33 and C34 are constants.

7. A system for estimating visceral fat area of a subject, comprising:
a data acquiring component for acquiring predetermined biological data of the subject including at least values indicating height and fat mass of the subject, and
a data processing component for estimating a value indicating visceral fat area of the subject based on the acquired biological data,
wherein the data acquiring component further acquires values indicating age and weight of the subject and wherein the data processing component estimates the value indicating visceral fat area by using an equation (3) as follows:

$$VFA = C31*FM/Ht^2 + C32*Age + C33*Wt/Ht^2 + C34 \quad (3)$$

where Ht is the value indicating height, Fm is the value indicating fat mass, VFA is the value indicating visceral fat mass, Age is the value indicating age, Wt is the value indicating weight, and C31, C32, C33 and C34 are constants.

8. A method for estimating visceral fat area of a subject, comprising the steps of:
acquiring predetermined biological data of the subject including at least values indicating height and fat mass of the subject, and
estimating a value indicating visceral fat area of the subject based on the acciuired biological data,
wherein values indicating age and body fat percentage of the subject are further acquired in the step of acquiring the biological data and wherein the estimation of the value indicating visceral fat area is performed by using an equation (5) as follows:

$$VFA = C51*FM/Ht^2 + C52*Age + C53* \% FAT + C54 \quad (5)$$

where Ht is the value indicating height, FM is the value indicating fat mass, VFA is the value indicating visceral fat mass, Age is the value indicating age, % FAT is the value indicating body fat percentage, and C51, C52, C53 and C54 are constants.

9. A system for estimating visceral fat area of a subject, comprising:
a data component for acquiring predetermined biological data of the subject including at least values indicating height and fat mass of the subject, and
a data processing component for estimating a value indicating visceral fat area of the subject based on the acciuired biological data,
wherein the data acquiring component further acquires values indicating age and body fat percentage of the subject and wherein the data processing component estimates the value indicating visceral fat area by using an equation (5) as follows:

$$VFA = C51*FM/Ht^2 + C52*Age + C53* \% FAT + C54 \quad (5)$$

where Ht is the value indicating height, Fm is the value indicating fat mass, VFA is the value indicating visceral fat mass, Age is the value indicating age, % FAT is the value indicating body fat percentage, and C51, C52, C53 and C54 are constants.

10. A system for estimating visceral fat area of a subject, comprising:
a data acquiring component for acquiring predetermined biological data of the subject including at least values indicating height and fat mass of the subject, and
a data processing component for estimating a value indicating visceral fat area of the subject based on the acquired biological data,
wherein the data processing component estimates the value indicating visceral fat area by using a parameter expressed as $Ht^2/FM$, where Ht is the value indicating height and FM is the value indicating fat mass.

11. The system of claim 10, wherein the data acquiring component further acquires a value indicating age of the subject and wherein the data processing component estimates the value indicating visceral fat area by using an equation (2) as follows:

$$VFA = C21*Ht^2/FM + C22*Age + C23 \quad (2)$$

where VFA is the value indicating visceral fat mass, Age is the value indicating age, and C21, C22 and C23 are constants.

12. The system of claim 10, wherein the data acquiring component further acquires values indicating age and weight of the subject and wherein the data processing component estimates the value indicating visceral fat area by using an equation (4) as follows:

$$VFA = C41*Ht^2/FM + C42*Age + C43*Wt/Ht^2 + C44 \quad (4)$$

where VFA is the value indicating visceral fat mass, Age is the value indicating age, Wt is the value indicating weight, and the $C_{41}$, $C_{42}$, $C_{43}$ and $C_{44}$ are constants.

13. The system of claim 10, wherein the data acquiring component further acquires values indicating age and body fat percentage of the subject and wherein the data processing component estimates the value indicating visceral fat area by using an equation (6) as follows:

$$VFA = C_{61} * Ht^2/FM + C_{62} * Age + C_{63} * \%FAT + C_{64} \qquad (6)$$

where VFA is the value indicating visceral fat mass, Age is the value indicating age, %FAT is the value indicating body fat percentage, and $C_{61}$, $C_{62}$, $C_{63}$ and $C_{64}$ are constants.

14. A system for estimating visceral fat area of a subject, comprising:
  a data component for acquiring predetermined biological data of the subject including at least values indicating height and fat mass of the subject, and
  a data processing component for estimating a value indicating visceral fat area of the subject based on the acquired biological data,
  wherein the data acquiring component further acquires a value indicating age of the subject and wherein the data processing component estimates the value indicating visceral fat area by using an equation (1) as follows:

$$VFA = C_{11} * FM/Ht^2 + C_{12} * Age + C_{13} \qquad (1)$$

where Ht is the value indicating height, FM is the value indicating fat mass, VFA is the value indicating visceral fat mass, Age is the value indicating age, and $C_{11}$, $C_{12}$ and $C_{13}$ are constants.

* * * * *